(12) United States Patent
Medin

(10) Patent No.: US 10,537,404 B2
(45) Date of Patent: Jan. 21, 2020

(54) DIRECTIONAL GUIDE FOR AN AIR-WATER SYRINGE TIP

(71) Applicant: Kristine J. Medin, Solon, IA (US)

(72) Inventor: Kristine J. Medin, Solon, IA (US)

(*) Notice: Subject to any disclaimer, the term of this patent is extended or adjusted under 35 U.S.C. 154(b) by 0 days.

(21) Appl. No.: 15/881,330

(22) Filed: Jan. 26, 2018

(65) Prior Publication Data

US 2018/0214245 A1 Aug. 2, 2018

Related U.S. Application Data

(60) Provisional application No. 62/452,062, filed on Jan. 30, 2017.

(51) Int. Cl.
*A61C 17/02* (2006.01)
*A61C 1/08* (2006.01)
*A61C 17/022* (2006.01)

(52) U.S. Cl.
CPC .......... *A61C 1/082* (2013.01); *A61C 17/0202* (2013.01); *A61C 17/022* (2013.01); *A61C 17/0217* (2013.01)

(58) Field of Classification Search
CPC . A61C 17/0217; A61C 17/0202; A61C 17/02; A61C 17/0211; A61B 1/0051; A61B 1/0052

See application file for complete search history.

(56) References Cited

U.S. PATENT DOCUMENTS

| 4,975,054 | A | * | 12/1990 | Esrock | A61C 17/0217 433/126 |
| 5,125,835 | A | | 6/1992 | Young | |
| 5,242,300 | A | * | 9/1993 | Esrock | A61C 17/0202 433/126 |
| 5,474,450 | A | | 12/1995 | Chronister | |
| 6,319,195 | B1 | * | 11/2001 | Nakaichi | A61B 1/0052 600/120 |
| 6,432,043 | B2 | * | 8/2002 | Nakaichi | A61B 1/0051 600/120 |
| 2013/0224681 | A1 | | 8/2013 | Smith | |
| 2016/0310247 | A1 | | 10/2016 | Wang et al. | |

OTHER PUBLICATIONS

International Searching Authority; Notification of Transmittal of the International Search Report and the Written Opinion of the International Searching Authority; of PCT Appl. No. PCT/US2018/015853 dated Apr. 5, 2018; 6 pages.

* cited by examiner

*Primary Examiner* — Ralph A Lewis
(74) *Attorney, Agent, or Firm* — Hamilton IP Law, PC; Jay R. Hamilton; Charles A. Damschen

(57) ABSTRACT

A directional guide for use with an air-water tip for a syringe includes an elongated member fixedly attached to a longitudinal section of the air-water tip. Extending outwardly from the elongated member is a position control member. The position control member is formed and positioned to rotate the elongated member and the air water tip together and to selectively activate air-water buttons on a syringe.

6 Claims, 2 Drawing Sheets

DIRECTIONAL GUIDE FOR AN AIR-WATER SYRINGE TIP

CROSS REFERENCE TO RELATED APPLICATION

This application claims the benefit to Provisional Application U.S. Ser. No. 62/452,062 filed on Jan. 30, 2017.

BACKGROUND OF THE INVENTION

This invention is directed to a directional guide and more particularly to a directional guide for an air-water syringe tip.

Air-water syringes are well-known in the art of dentistry and are used to provide water or air to a patient's mouth during a dental procedure. Presently, a number of air-water syringes utilize disposable tips that are removably connected to the syringe, as well as their metal counter-parts. While useful, there are problems that still exist with either type of tip, metal or plastic disposable. For example, because the tip rotates freely with respect to the syringe, it is difficult to position the tip with one hand with respect to the patient's mouth or hold the tip in a stationary position for retraction of tissue (i.e. tongue, cheek). Also, to move the tip while spraying air or water requires two hands. One hand is needed to adjust the syringe tip position out of the mouth before use, while the other hand operates the syringe with regards to air-water. Thus, there is a need in the art for a device that addresses this problem.

An objective of the present invention is to provide a directional guide that assists in holding an air-water tip in a stationary position.

Another objective of the present invention is to provide a directional guide that permits one to move an air-water tip while spraying using only one hand.

These and other objectives will be apparent to those skilled in the art based upon the following written description, drawing, and claims.

SUMMARY OF THE INVENTION

A directional guide is used to position an air-water tip attached to a syringe during a dental procedure. The directional guide includes an elongated member fixedly attached to a section of the air-water tip.

Extending outwardly from the elongated member is a position control member. The position control member is formed and positioned to permit a technician, using one hand to hold the syringe and the thumb of the same hand to position and hold the air-water tip in a selected position and concurrently activate the air-water buttons on the syringe if needed.

DETAILED DESCRIPTION OF THE PREFERRED EMBODIMENT

Figure 1:
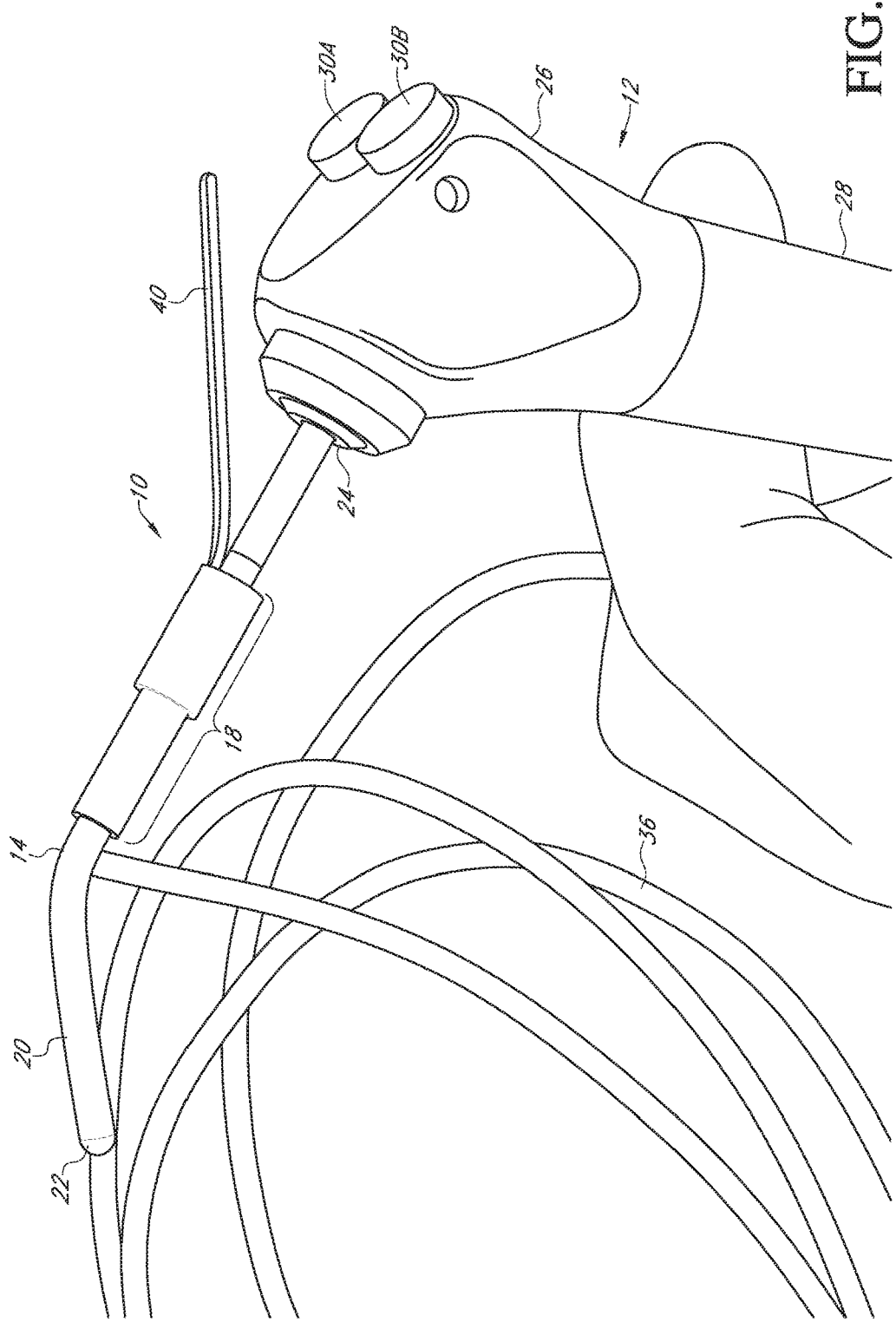
FIG. 1 is a perspective view of a directional guide for an air-water tip and syringe.
Figure 2:
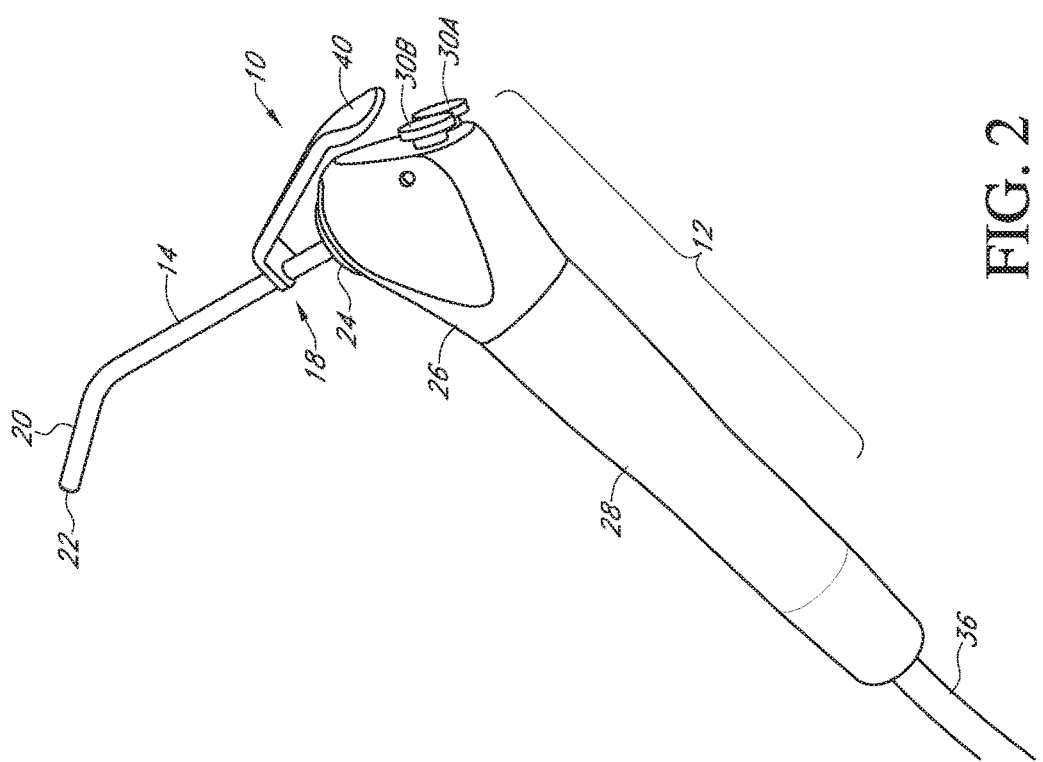
FIG. 2 is a perspective view of a directional guide for an air-water tip and syringe.

Referring to the Figure, a directional guide 10 for an air-water tip 14 connected to section 18 of the tip 14. The directional guide 10 includes an elongated member 18 that is fixed onto the air-water tip 14 longitudinally between an angled section 20 of the tip 14 and a second end 24 of the tip 14.

The syringe 12 has a head section 26 and a body section 28. The head section 26 has a pair of activation buttons 30A and 30B for selectively releasing air or water. An air-water line 36, carries both pressurized air and pressurized water, and extends from the syringe 12 to a source of pressurized air and water. The air line and water line 36 is connected to the head 26 of the syringe to deliver air or water to the tip 14 upon activation of the air 30A or water 30B buttons.

Extending outwardly from the fixed attachment 18 of the directional guide 10 is a position control member 40. The position control member 40 is of any size, shape, or structure. In one example, the position control member 40 extends upwardly from the fixed attachment 18 and backwardly toward and above the head section 26 of the syringe. Preferably, the position control member 40 is made of rigid material that upon application of a downward manual force in relation to the syringe, permits the stationary position of the syringe tip or horizontal force to move the tip from side to side.

The fixed attachment 40 is connected to the section 18 of the tip 14 in a fixed manner such that the directional guide 10 and tip 14 rotate together in relation to the head section 26 of the syringe 12. In operation, a technician holds the handle section 28 in their palm and wrap their fingers around the hand section 28. The technician's thumb is used to selectively activate the air-water buttons 30A 30B or the position of the tip 14. More specifically, using their thumb, the technician moves the position control member 40 selectively in a 180 degree motion in relation to the sides of the head section 26. As the position control member 40 moves, the tip 14 rotates in relation to the head section of 26 of the syringe 12. When the tip 14 is at a desired position (i.e. angle) in relation to a patient's mouth, the technician is then able to direct air-water in the proper direction that is desired by pushing desired air 30A or water 30B button. When the position control member 40 is held with downward force the tip 14 is fixated in a desired position allowing the technician to properly retract tissue (i.e. tongue, cheek) without losing position or proper retraction due to free rotation of the tip 14.

Thus, a directional guide has been disclosed where the tip of an air-water syringe is either rotated to proper position or held and fixated in one desired position with one hand based on need of syringe for either air-water or retraction.

What is claimed is:

1. A syringe comprising:
   a. a head section;
   b. a plurality of activation buttons positioned on said head section;
   c. a handle section engaged with said head section;
   d. an air-water tip having a first end and a second end, wherein said second end is pivotally engaged with said head section;
   e. a directional guide comprising:
      i. a fixed attachment portion, wherein said fixed attachment portion is secured to said air-water syringe tip between said first and second ends of said air-water tip;
      ii. a position control member, wherein said position control member extends outwardly from said fixed attachment portion, and wherein said position control member extends upwardly and backwardly toward and above said head section of said syringe.

2. The syringe according to claim 1 wherein said directional guide is further defined as rotating with said air-water syringe tip in relation to said head section of said syringe.

3. The syringe according to claim 2 wherein a rotational movement of said air-water syringe tip occurs by applying a manual force from a thumb of a technician on said position control member.

4. The syringe according to claim 1 wherein said position control member is further defined as being made of a rigid material.

5. The syringe according to claim 1 wherein said position control member is further defined as being controlled by a thumb of an operator.

6. The syringe according to claim 1 wherein said position control member is further defined as being positioned with respect to said head section of said syringe to permit a technician to hold said handle section of said syringe in a hand of said technician and use a thumb of said hand to selectively activate any one of said plurality of activation buttons on said head section of said syringe, rotate said syringe, or hold said syringe in a stationary position.

\* \* \* \* \*